United States Patent [19]

Hastings et al.

[11] Patent Number: 5,450,853
[45] Date of Patent: Sep. 19, 1995

[54] PRESSURE SENSOR

[75] Inventors: Roger Hastings; Ken Larson, both of Maple Grove, Minn.

[73] Assignee: Scimed Life Systems, Inc., Maple Grove, Minn.

[21] Appl. No.: 141,134

[22] Filed: Oct. 22, 1993

[51] Int. Cl.6 .......................................... A61B 5/0215
[52] U.S. Cl. ..................................... 128/675; 128/748; 73/749
[58] Field of Search ............................... 128/672–675, 128/748; 73/749

[56] References Cited

U.S. PATENT DOCUMENTS

| | | |
|---|---|---|
| 2,769,337 | 11/1956 | Rich . |
| 3,062,202 | 11/1962 | Hyman et al. . |
| 3,349,623 | 10/1967 | Pastan . |
| 3,357,260 | 12/1967 | Detalle . |
| 3,750,067 | 7/1973 | Fletcher et al. ............... 335/296 |
| 3,911,902 | 10/1975 | Delpy . |
| 3,942,382 | 3/1976 | Hök . |
| 4,261,208 | 4/1981 | Hök . |
| 4,297,890 | 11/1981 | Hök . |
| 4,413,528 | 11/1983 | Hök et al. . |
| 4,462,259 | 7/1984 | Stoltman et al. ............... 73/749 |
| 4,487,206 | 11/1984 | Aagard . |
| 4,691,709 | 9/1987 | Cohen . |
| 4,711,249 | 12/1987 | Brooks . |
| 4,722,218 | 2/1988 | Strader . |
| 4,780,418 | 10/1988 | Kratzer . |
| 4,809,709 | 3/1989 | Brooks . |
| 4,846,191 | 7/1989 | Brockway et al. . |
| 4,854,326 | 8/1989 | Merrick . |
| 4,874,005 | 10/1989 | Potter ............................. 137/85 |
| 4,887,610 | 12/1989 | Mittal . |
| 4,924,872 | 5/1990 | Frank . |
| 4,924,877 | 5/1990 | Brooks . |
| 4,953,553 | 9/1990 | Tremulis ...................... 128/673 X |
| 4,991,590 | 2/1991 | Shi . |
| 5,050,297 | 9/1991 | Metzger . |
| 5,113,868 | 5/1992 | Wise et al. . |
| 5,178,153 | 1/1993 | Einzig . |
| 5,178,159 | 1/1993 | Christian . |
| 5,195,375 | 3/1993 | Tenerz et al. . |
| 5,226,423 | 7/1993 | Tenerz et al. . |

FOREIGN PATENT DOCUMENTS

0548872A1 6/1993 European Pat. Off. .

OTHER PUBLICATIONS

Chau, H. L., et al., "An Ultraminiature Solid–State Pressure Sensor for a Cardiovascular Catheter", IEEE Transactions on Electron Devices, vol. 35, No. 12, pp. 2355–2362, Dec. 1988.

Author unknown, "On the Spot: Sensor That Measures Blood Pressure", one page, date unknown.

Product Literature from RADI Medical Systems on their "Pressure Guide 0.018: Guidewire-Mounted Pressure Sensor for PTCA", 2 pages, date unknown.

Author unknown, "Pressure Gradient Analyzer Guidewire-Mounted Sensor", Biomedical Technology Information Service, p. 210, Oct. 15, 1991.

Product Literature from Cardiometrics on their "Flo-Wire" and FloMap, 2 pages, date unknown.

Primary Examiner—Angela D. Sykes
Attorney, Agent, or Firm—Willian, Brinks, Hofer, Gilson & Lione

[57] ABSTRACT

A pressure sensor having a tubular member partially filled with a ferrofluid column and partially filled with air, with an electrically conductive coil wrapped around the tubular member. When in use, the coil has alternating current running therethrough and the voltage across the coil is monitored. Physiologic pressure variations result in proportional variations in the position of the ferrofluid/air interface relative to the coil. This results in proportional changes in the coil voltage due to the change in coil inductance. The pressure sensor is compact and can be incorporated into many devices including a guide wire.

21 Claims, 4 Drawing Sheets

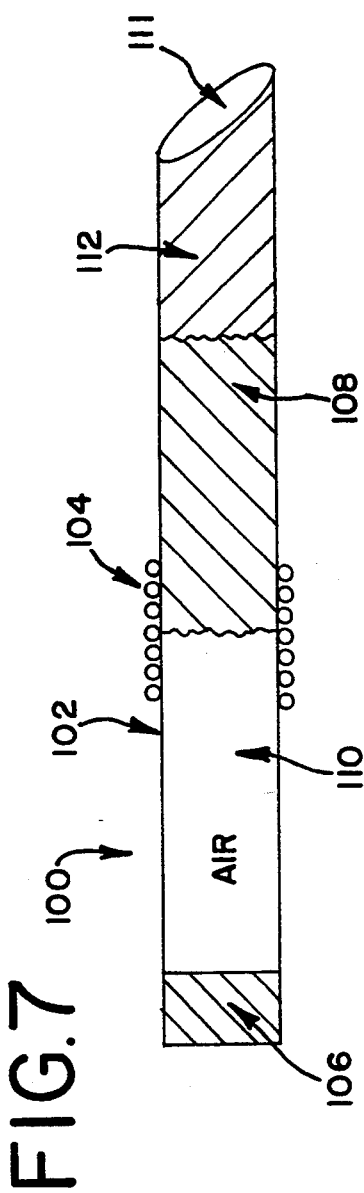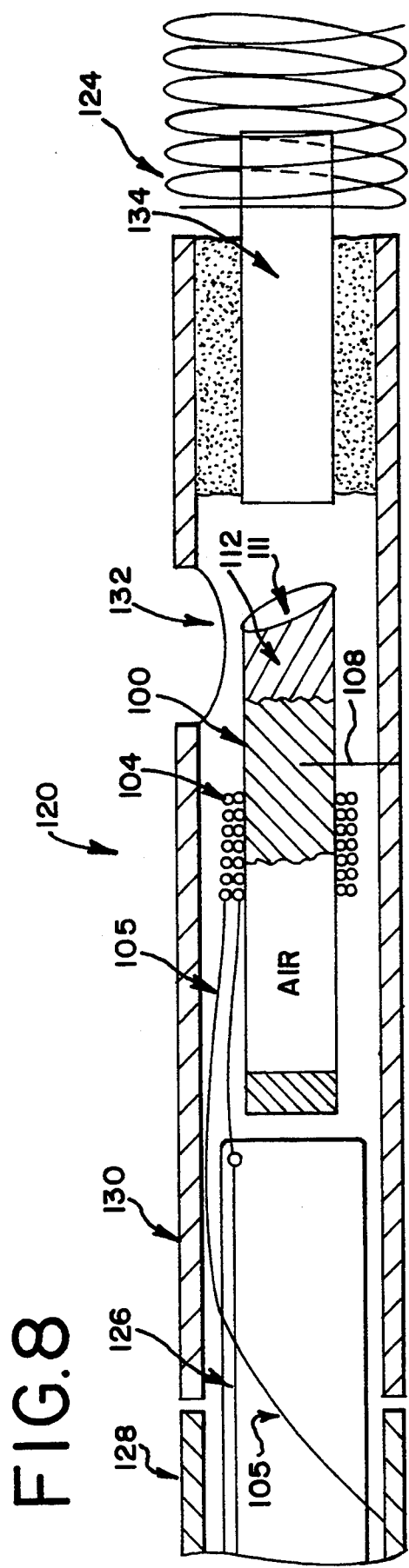

PRESSURE SENSOR

FIELD OF THE INVENTION

The invention relates to a pressure sensor, and more particularly, a pressure sensor for measuring the change in voltage across a coil caused by the movement of a column of ferrofluid.

BACKGROUND OF THE INVENTION

Angioplasty procedures have gained wide acceptance in recent years as efficient and effective methods for treating types of vascular disease. In particular, angioplasty is widely used for opening stenoses in the coronary arteries although it is also used for the treatment of stenoses in other parts of the vascular system.

The most widely used form of angioplasty makes use of a dilation catheter which has an inflatable balloon at its distal end. Inflation of the balloon at the site of the occlusion causes a widening of the lumen to reestablish an acceptable blood flow thorough the lumen.

Often it is desirable to determine the severity of the occlusion in order to properly chose a dilation catheter. Various techniques have been used to determine the severity of the occlusion. One way of determining the severity of the occlusion is to measure pressure both proximal to and distal of the stenoses. Devices that are used for this purpose include catheter-like members with some type of pressure sensing device incorporated therein. One known device measures the pressure as a function of the deflection of a diaphragm located at either the proximal or distal ends of the catheter. Positioning the sensing part of the sensing device at the proximal end of the catheter can introduce measuring inaccuracies due to the catheter length. Positioning the sensing part of the sensing device at the distal end of the catheter requires the sensing device to be made extremely small. Otherwise, the sensing device will impede the blood flow and affect the pressure reading. It is desirable to provide a pressure sensor that is compact so that it can be delivered to narrow sites while having a high degree of accuracy.

Other known devices, for example, those disclosed in Delpy (U.S. Pat. No. 3,991,902) and Hök (U.S. Pat. No. 3,349,623), measure the change in capacitance or resistance caused by the displacement of a liquid/gas interface.

SUMMARY OF THE INVENTION

According to a first aspect of the invention, there is provided a pressure sensor having a tubular member having a proximal end, a distal end and a window exposing the interior of the tubular member to the exterior of the tubular member; a column of ferrofluid partially filling the interior of the tubular member, the ferrofluid column capable of movement within the tubular member in response to pressure exerted at the window of the tubular member; and a transducer for converting the movement of the ferrofluid column in the tubular member into a signal proportional to the pressure exerted at the window.

According to another aspect of the invention, there is provided a method of obtaining information about a patient's anatomy by providing a pressure sensor including a tubular member having a proximal end, a distal end and a window exposing the interior of the tubular member to the exterior of the tubular member; a column of ferrofluid partially filling the tubular member, the ferrofluid column capable of movement within the tubular member in response to pressure exerted at the window of the tubular member; and a transducer for converting the movement of the ferrofluid column in the tubular member into a signal proportional to the pressure exerted at the window. The pressure sensor is inserted into the patient's vessel and positioned so that the window of the pressure sensor is located at a desired location. A constant drive current is applied to the transducer and the voltage across the transducer is measured and converted into a pressure value and displayed.

The invention itself together with objects and attendant advantages, will best be understood by reference to the following detailed description taken in conjunction with accompanying drawings. It should be understood, however, that this description is to be illustrative rather than limiting, the scope of the invention being defined by the appended claims and equivalents thereof.

BRIEF DESCRIPTION OF THE DRAWINGS

FIG. 7 illustrates a schematic of a pressure sensor according to another embodiment of the present invention.

FIG. 8 illustrates a cross-sectional view of the sensor of FIG. 7 incorporated in a guide wire.

DETAILED DESCRIPTION OF TEE PRESENTLY PREFERRED EMBODIMENTS

Figure 1:
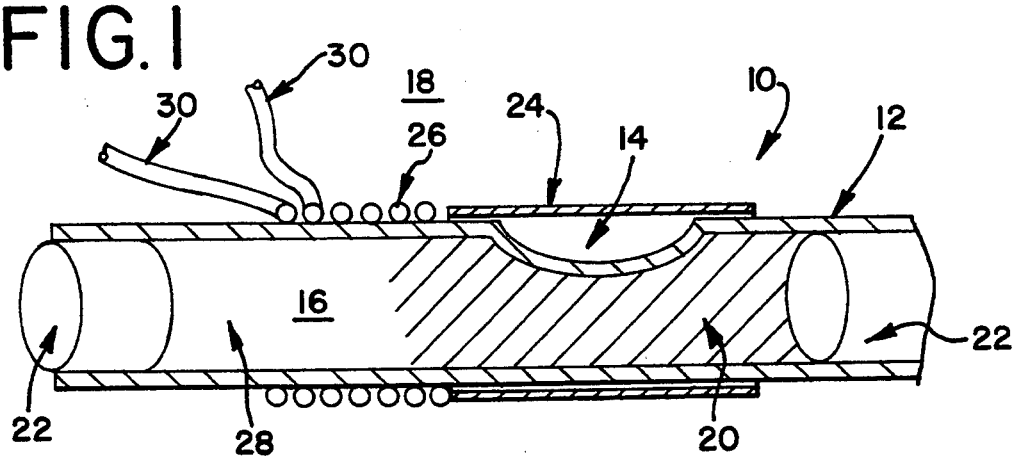
FIG. 1 illustrates a cross-sectional view of a first embodiment of a pressure sensor according to the present invention.

FIG. 1 illustrates a cross-sectional view of a first embodiment of a pressure sensor according to the present invention. The pressure sensor 10 includes a tubular member 12 having a window or opening 14 cut out of one side. The window 14 exposes the interior 16 of the tube to the exterior 18 of the tube. A portion of the interior 16 of the tubular member 12 is filled with a ferrofluid column 20 and the remainder is filled with air. Each end of the tubular member is sealed with a plug 22 to create a closed volume within the interior of the tubular member 12. A sheath 24 surrounds a portion of the exterior 18 of the tubular member 12. In particular, the sheath 24 completely covers the window 14 formed in the tubular member 12. A coil 26 is wound around a portion of the exterior 18 of the tubular member 12. The coil 26 is located proximal to the sheath 24, the term proximal indicating towards the left of the diagram and the term distal indicating towards the right of the diagram. The coil 26 has leads 30 which are used to connect the coil 26 to an electronic circuit which will be described in detail with reference to FIG. 2. As previously described, the ferrofluid column 20 fills portion of the interior of the tubular member 12 and the remainder of the closed volume is filled with air creating an air column 28.

In a preferred embodiment, the various pieces of the sensor 10 are formed of the following materials and have the following dimensions. Other materials and different dimensions may be used not only in the presently described embodiment, but in all embodiments of the present invention. The present invention is not limited to the disclosed materials or dimensions. The tubular mender 12 is formed from a polyimide tube having a length of about 0.2 inches, an outer diameter of about 0.0071 inches and an inner diameter of about 0.0056 inches. The sheath 24 is formed of polyester having a length of about 0.075 inches and a thickness of about 0.00018 inches. The coil 26 is formed of 50 gauge insulated silver wire wound in two layers having 80 turns per layer to create a coil length of about 0.1 inches. The sensor 10 has a maximum outer diameter located at the coil 26 of about 0.011 inches. The plugs 22 are formed of nickel titanium (NiTi) and have a diameter of about 0.005 inches which allows the plugs 22 to securely seal the ends of the tubular member 12. The ferrofluid column 20 occupies a volume of about $4 \times 10^{-6}$ cubic inches and has a length of about 0.15 inches. Ferrofluid, as those skilled in the art know, is a suspension of iron filings. Preferably, the ferrofluid 20 used is commercially available from Ferrofluidics of Nashua, N.H. Preferably, part EMG 905 is used because it has a low viscosity and a high magnetic permeability. The operation of the sensor will be described after the electronics have been described.

Figure 2:
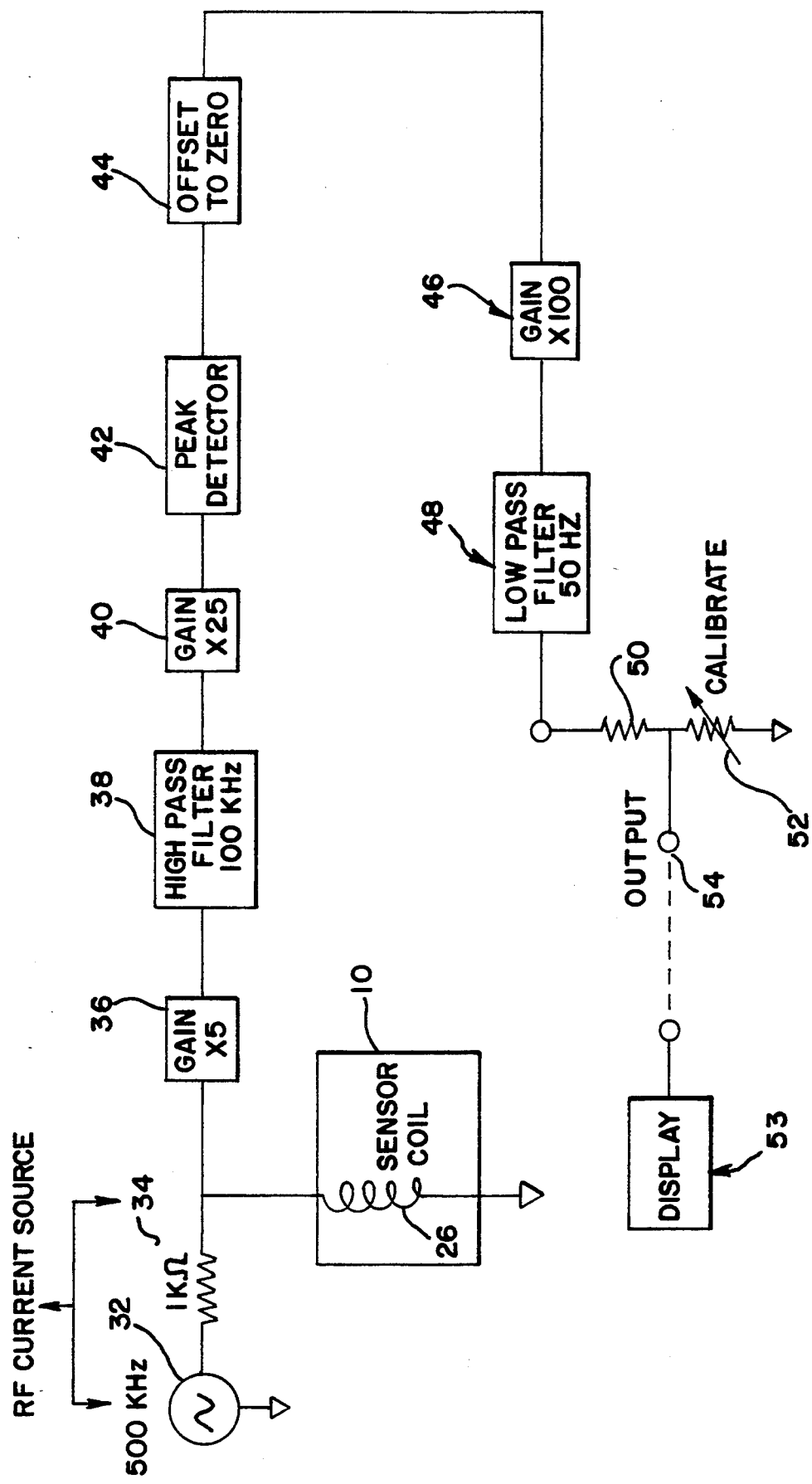
FIG. 2 illustrates in schematic the electronics used in conjunction with the sensors of the present invention.

FIG. 2 illustrates in schematic the electronics used in conjunction with the sensors of the present invention. The electronics include a variable frequency generator 32 connected to one end of a resistor 34. The other end of the resistor 34 is connected to the coil 26 of the sensor 10, represented in schematic as a block via the coil leads 30 and to an input of a gain circuit 36. The output of the gain circuit 36 is connected to a high pass filter 38 which is connected to another gain circuit 40. The output of the gain circuit 40 is connected to a peak detector circuit 42. The output of the peak detector circuit 42 is connected to an offset circuit 44 and the output of the offset circuit 44 is connected to the input of another gain circuit 46. The output of the gain circuit 46 is applied to the input of a low pass filter 48. The output of the low pass filter 48 is connected to ground through a resistor 50 and a potentiometer 52. An output 54 is taken after the resistor 50 but before the potentiometer 52. The output 54 is connected to a display device 53.

In a preferred embodiment, the variable frequency generator generates an alternating current signal having a frequency of about 500 kilohertz (kHz). The resistor 34 is about 1 kOhm (k$\Omega$), the resistor 50 is about 100 k$\Omega$ and the potentiometer has a maximum resistance of about 100 k$\Omega$. Gain circuit 36 has a gain of about 5, gain circuit 40 has a gain of about 25 and gain circuit 46 has a gain of about 100. The high pass filter 38 has a corner frequency of about 100 kHz and the low pass filter has a corner frequency of about 50 Hertz (Hz). The display device 53 can be in the form of an oscilloscope, voltmeter, graphics display, chart recorder or any other type of display or peripheral device that would be helpful to the user of the sensor. The voltage measured across the coil of the sensor is thus converted by the circuitry of FIG. 2 to provide a pressure measurement. The components forming the electronics of the present invention are formed from conventional devices well known to those skilled in the art and thus need not be described in greater detail. Of course, the electronics shown in FIG. 2 would be contained in a suitable housing.

Figure 3:
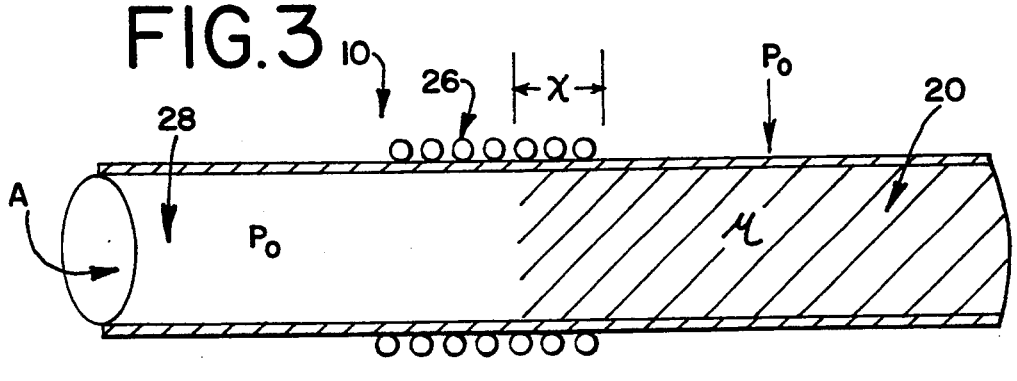
FIG. 3 illustrates a schematic of the pressure sensor at an initial condition where the sensor is exposed to ambient pressure.

The principle of operation of the pressure sensor of FIG. 1 in combination with the electronics of FIG. 2 will now be described. Thereafter, other embodiments of the pressure sensor will be described with reference to FIGS. 5-8. FIG. 3 illustrates a schematic of the pressure sensor at an initial condition where the sensor is exposed to ambient pressure $P_0$. While the window 14 of the sensor has not been illustrated, exerted pressure $P_0$ is shown acting on the pressure sensor where the window would be located. The proximal interior of the sensor is filled with a column of air 28 having a length L a cross section A. The air column 28 is at ambient pressure $P_0$. The remaining distal portion of the sensor is filled with the ferrofluid column 20 having a permeability of $\mu$. The coil 26 has a length l comprised of N turns. The coil is positioned so that a distal length x surrounds the ferrofluid column 20. Initially, the inductance in the coil $\mathcal{L}_0$ is described by equation (1);

$$\mathcal{L}_0 = \mu_0 \mu N^2 (Ax/l), \qquad (1)$$

where $\mu_0$ is the permeability of free space.

The pressure $P_0$ in the air column is described by the gas law equation (2);

$$P_0 = CT/V = CT/AL, \qquad (2)$$

where V is the volume of the air column 28, C is a constant and T is temperature in degrees Kelvin.

Figure 4:
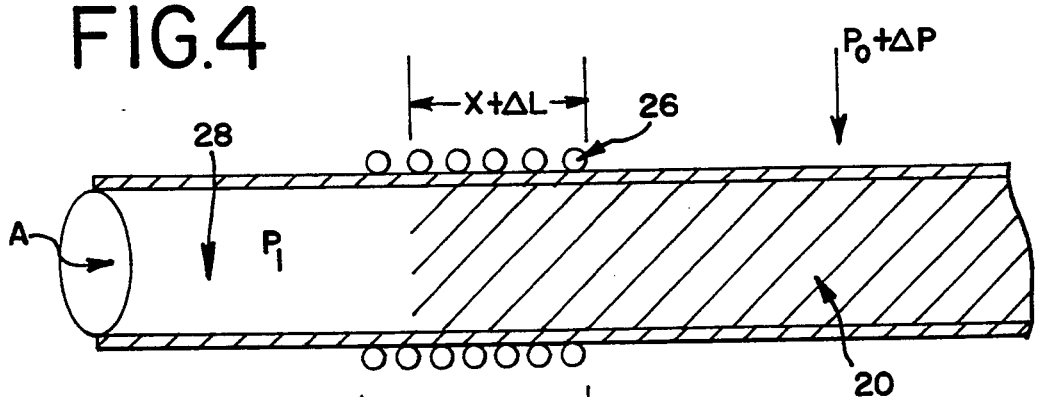
FIG. 4 illustrates a schematic of the pressure sensor exposed to an external pressure.

When an external pressure, $P_0 + \Delta P$, is exerted at the window of the sensor 10, the ferrofluid column 20 is displaced a distance $\Delta L$ in the proximal direction. FIG. 4 illustrates a schematic of the pressure sensor exposed to such an external pressure. The displacement of the ferrofluid column causes an equal displacement of the air column 28 thereby increasing the pressure of the air column 28. The window material is chosen so that force exerted on the ferrofluid column by the compressed air column is much larger and dominates the elastic restoring force of the window. From equation (2), increased pressure $P_1$ of the air column 28 is described by equation (3)

$$P_1 = CT/(A(L - \Delta L)) \qquad (3)$$

By making the approximation that the ratio of $\Delta L$ to L is much less than 1 ((i.e. $\Delta L/L << 1$) equation (3) can be reduced to equation (4).

$$P_1 = P_0 + P_0(\Delta L/L) = P_0 + \Delta P \qquad (4)$$

From equation (4) it is apparent that the ratio of $\Delta L$ to L is approximately the same as the ratio of $\Delta P$ to $P_0$ ( i.e. $\Delta L/L = \Delta P/P_0$) .

Inductance in the coil is described by equation (6);

$$\mathcal{L} = \mu_0 \mu N^2 (A/l)(Z/l) \qquad (6)$$

where Z equals the length of ferrofluid column surrounded by the coil. With reference to FIG. 4, Z equals $x + \Delta L$ and the inductance of the coil is described by equation (7).

$$\mathcal{L} = \mu_0 \mu N^2 (A/l)(x + \Delta L)/l) \qquad (7)$$

Using equation (1) , equation (7) can be reduced to equation (8).

$$\mathcal{L} = \mathcal{L}_0 + \mathcal{L}_0(\Delta L/l) = \mathcal{L}_0 + \mathcal{L}_0(L/l)(\Delta P/P_0) \quad (8)$$

The voltage across the coil 26 for a constant drive current I is measured by the electronics of Figure 2. For a constant current I applied to the coil, the voltage across the coil is described by equation (9).

$$V = I\sqrt{R^2 + \omega^2 \mathcal{L}^2}, \quad (9)$$

where $\omega$ is proportional to the frequency of the signal applied by generator 32 of FIG. 2, R is the resistance of the coil and $\mathcal{L}$ is the inductance of the coil. Thus the voltage is dependent upon both the resistance of the coil and its inductance.

Substituting equation (8), equation (9) is described by equation (10).

$$V = I\sqrt{R^2 + \omega^2 \mathcal{L}_0^2 (1 + (\omega^2 \mathcal{L}_0^2 /(R^2 + \omega^2 \mathcal{L}_0^2))(L/l)(\Delta P/P_0))} \quad (10)$$

Eliminating the offset represented by the term $$I\sqrt{R^2 + \omega^2 \mathcal{L}_0^2}$$

the change in voltage, V, is described by equation (11).

$$\Delta V = ((I\omega^2 \mathcal{L}_0^2 / \sqrt{R^2 + \omega^2 L_0^2})(\mathcal{L}/l)(\Delta P/P_0)) \quad (11)$$

From equation (11) it can be seen that the change in voltage, $\Delta V$, is linearly proportional to the change in pressure $\Delta P$. In summary, an alternating current is passed through the coil of the sensor and the voltage across the coil is monitored. Physiologic pressure variations result in proportional variations in the position of the ferrofluid column relative to the coil. This results in proportional changes in the coil voltage due to the change in the coil's inductance caused by the movement of the ferrofluid column.

Changes in temperature, otherwise known as temperature drift, affect both the resistance and inductance of the coil and thus affect the measured voltage across the coil, To compensate for the effects of temperature drifts the following adjustments are made which virtually eliminate the effects of temperature drift on the voltage measured across the coil. It has been found that the effects of temperature change on the resistance and the inductance of the coil are opposite. That is to says as one increases the other decreases and vice versa. The effect of temperature change is described by equation (12).

$$dV/dT = I((dV/dR)(dR/dT) + (dV/D\mathcal{L})(d\mathcal{L}/dT)) \quad (12)$$

Using equation (9), equation (12) is expanded to equation (13).

$$dV/dT = (IR/\sqrt{R^2 + \omega^2 \mathcal{L}^2})(dR/dT) + ((I\omega^2 \mathcal{L})/\sqrt{R^2 + \omega^2 \mathcal{L}^2})(d\mathcal{L}/dT) \quad (13)$$

Because the coil is preferably formed of a silver wire, the term dR/dT is a positive constant. In addition, using equation (6), the term $d\mathcal{L}/dT$ can be described by equation (14):

$$d\mathcal{L}/dT = \mathcal{L}_0(1/x)(dx/dT) = -\mathcal{L}_0(1/x)(dL/dt) \quad (14)$$

Using the gas law of equation (2), equation (14) is further reduced to equation (15).

$$d\mathcal{L}/dT = -\mathcal{L}_0/T(L/x) \quad (15)$$

Using equation (15), equation (13) is reduced to equation (16).

$$dV/dT = (IR/\sqrt{R^2 + \omega^2 \mathcal{L}^2})[(dR/dT) - (\omega^2 \mathcal{L}^2/R)(L/x)(1/T)] \quad (16)$$

The frequency, $\omega$, of generator 32 is adjusted to yield a zero drift (i.e., dV/dT=0), or stated differently dR/dT=(($\omega\mathcal{L}$)²/(RT))(L/x) or ($\omega\mathcal{L}$/R)²=(x/L)(T/R)(dR/dT).

For silver, the term (1/R)(dR/dT) is equal to about 0.0038/° K., body temperature is about 310° K. and x/L is approximately 0.5. Thus $\omega\mathcal{L}$/R is equal to about 0.8. In a preferred embodiment, R is about 6Ω and $\mathcal{L}$ is about 1.5 μH. Since $\omega = 2\pi f$ where f is frequency in Hertz, we find f is about equal to 510 kHz which is close to the experimentally found frequency at which the sensor thermal drift is equal to zero.

In summary, R increases with an increase in temperature while $\mathcal{L}$ decreases with an increase in temperature because as the temperature increases, air column 28 expands and pushes the ferrofluid column distally out from under the coil 26. The impedance of the coil is resistive at low frequencies and inductive at high frequencies. Thus a frequency exists for which the resistive and inductive thermal drifts cancel to zero.

Figure 5:
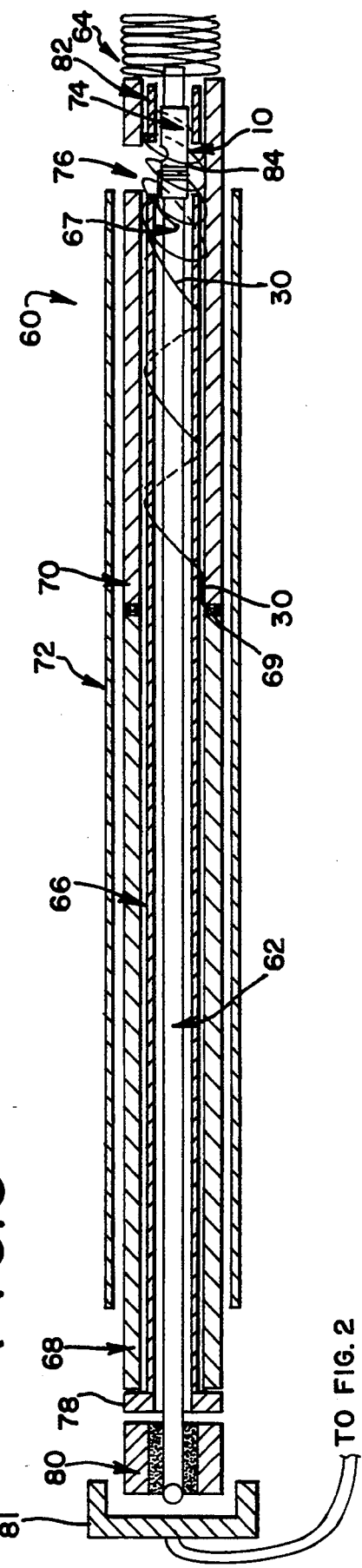
FIG. 5 illustrates a cross-sectional view of the pressure sensor of FIG. 1 incorporated in a guide wire.

FIG. 5 illustrates a cross sectional view of the pressure sensor of FIG. 1 incorporated in a guide wire 60. According to this embodiment, the guide wire 60 includes a core wire 62, a spring tip 64 having an extension member 74, a first sheath 66, a first tubular member 68, a second tubular member 70, a second sheath 72, a third sheath 82 and a coil 84. The pressure sensor 10 is located between the distal end of the core wire 62 and the proximal end of the extension member 74. In a preferred embodiment, neither the distal end of the core wire 62 nor the proximal end of the extension member 74 are coupled or physically joined to the sensor 10. Alternatively, a pliable glue may be used to bond the sensor to the core wire and extension member, however, preferably the sensor remains decoupled.

Surrounding and in contact with approximately the entire length of the core wire 62 is the first sheath 66. Surrounding and in contact with the extension member 74 is the third sheath 82. Surrounding a proximal portion of the core wire 62 and the first sheath 66 is the first tube 68. The proximal end of the second tube 70 is bonded to the distal end of the first tube 68 so that the second tube 70 surrounds the distal portion of the core wire 62, sensor 10, coil 84 and extension member 74. The second tubular member 70 has a window or opening 76 cut out on one side to expose the sensor 10 as will be described in detail hereinafter. The spring tip 64 is located distal to the distal end of the second tubular member 70. Surrounding and in contact with most of the first and second tubular members, 68 and 70, is the second sheath 72. Preferably, the second sheath terminates at the window 76 formed in the second tubular member 70.

Figure 6:
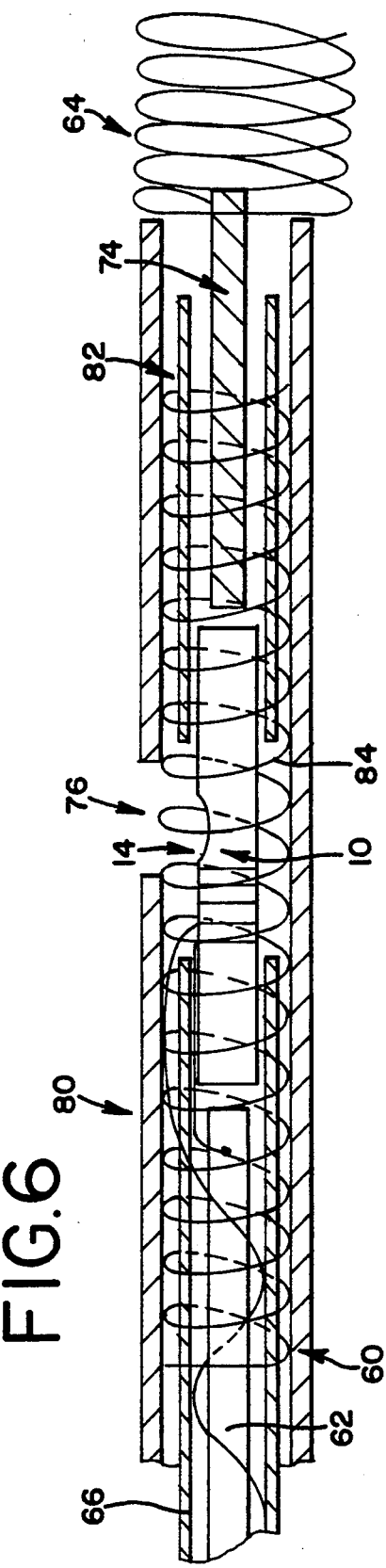
FIG. 6 illustrates in further detail a portion of the guide wire shown in FIG. 5.

The coil 84 surrounds the sensor and a portion of the first sheath 66 and the third sheath 82. A more detailed illustration of this section of the guide wire is shown in FIG. 6 and will be described hereinafter.

The proximal end of the spring tip 64 is bonded to extension member 74 preferably by soldering. One lead 30 of the coil 26 is soldered to the core member 62 at 67. The second lead 30 is wrapped around the exterior of the first sheath 66 and is soldered at 69 to the distal end of the first tubular member 68

At the proximal end of the first tubular member is an insulating spacer 78 bonded to the proximal end of the first tubular member 68 and the first sheath 66. Proximal to the insulating spacer 78 is a third tubular member 80 The third tubular member 80 is connected to the proximal portion of the core wire 62 preferably by a conductive epoxy.

In a preferred embodiment, the various components of guide wire 60 are formed from the following materials and have the following dimensions. Core wire 62 is formed from a gold plated stainless steel wire having a length of about 66 inches and a diameter of about 0.008 inches. The first sheath 66 is formed from an insulating material, preferably polyimide or polyester and has a length of about 65 inches. First tubular member 68 is formed of gold plated stainless steel tubing having a length of about 59 inches, an inner diameter of about 0.012 inches and an outer diameter of about 0.017 inches. The second tubular member 70 is formed from polyester or a blend of nylon and polyether or polyether block amide, commercially available under the tradename PEBAX from Autochem of Birdsboro, Pa. The second sheath 72 may be formed of polyester or alternatively, TEFLON may be coated over the first and second tubular members 68 and 70. The third tubular member 80 is formed by a gold plated stainless steel tube and has a length of about 1.0 inches, an inner diameter of about 0.012 inches and an outer diameter of about 0.017 inches.

As previously described, the leads 30 of sensor coil 26 are soldered to the core member 62 at 67 and first tubular member 68 at 69. Because the core member 62 and the first tubular member 68 are formed of gold plated stainless steel, they act as conductors which extend the leads to the proximal end of the guide wire. The proximal end of the first tubular member 68 and the third tubular member 80, separated from the first tubular member 68 by insulating spacer 78 are then used as contact points. A connector (not shown) is attached to the proximal end of the guide wire and the connector makes contact with the third tubular member 80 and the proximal end of the first tubular member 68. The connector connects the guide wire to the electronics of FIG. 2. Alternatively, the leads 30 may be extended the length of the guide wire to the guide wire's proximal end by any of the techniques described in U.S. Ser. No. 08/055,702, filed Apr. 29, 1993 entitled "Apparatus and Method For Performing Diagnostics and Intravascular Therapies", now U.S. Pat. N o. 5,346,508, issued Sep. 13, 1994, and U.S. Ser. No. 07/969,743, filed Oct. 30, 1992 entitled "Vibration Sensing Guidewire", now abandoned the entire disclosures of which are hereby specifically incorporated by reference.

Delivery of a guide wire to the site of an occlusion is well known by those skilled in the art and thus need not be described in detail. The guide wire 60 of FIG. 5 is delivered so that the window 76 formed in the second tubular member 70 is positioned proximal to the occlusion to expose the sensor 10 to the pressure existing in the vessel or artery at that location. The guide wire 60 is then moved to a location distal to the occlusion to measure the pressure at that location.

FIG. 6 illustrates in further detail a portion of the pressure sensor of FIG. 5. The third sheath 82 surround and contacts a portion of the sensor 10 distal to the sensor's window 14 and most of the extension member 74. Coil 84 surrounds the sensor 10 and extends both proximally and distally of the sensor to surround a portion of the first sheath 66 and a portion of the third sheath 82 In a preferred embodiment, the third sheath 82 is formed of polyimide and has a length of about 0.5 inches an inner diameter of about 0.008 inches and an outer diameter of about 0.010 inches. Coil 84 is formed of stainless steel wire having a diameter of about 0.002 inches and the coil 84 has a length of about 1.0 inches formed by 200 turns.

The coil 84 is provided for support over the sensor 10 to reduce forces that may be applied to the sensor 10 as the guide wire 80 is being delivered intravascularly.

FIG. 7 illustrates a schematic of a pressure sensor 100 according to another embodiment of the present invention. The pressure sensor 100 includes a tubular member 102 a sensor coil 104 and a plug 106. The plug is inserted into the proximal end of the tubular member to securely seal that proximal end. A distal portion of the interior of the tubular member is filled with a ferrofluid column 108 while the proximal portion of the interior of the tubular member is filled with air creating an air column 110. Unlike the sensor of FIG. 1, a window is not provided in the side of the tubular member 102 but rather the window 111 is formed by leaving the distal end of the tubular member 102 open. A non-volatile fluid 112 fills the distal most portion of the interior of the tubular member between the ferrofluid column 108 and the window 111 formed by the open distal end of the tubular member. The non-volatile fluid 112 acts as plug similar to the plug 106 at the proximal end of the sensor to prevent the evaporation of the ferrofluid when the sensor is not in use. In a preferred embodiment, the non-volatile fluid used is dioctylphthalate available from the Aldrich Chemical Company of Milwaukee, Wis. Apart from the described differences in construction, the pressure sensor 100 operates in a similar manner as previously described with reference to the other sensors.

FIG. 8 illustrates a cross-sectional view of the sensor of FIG. 7 incorporated in a guide wire 120. The guide wire 120 includes a core wire 122, a spring tip 124, a sleeve 126, a first tubular member 128 and a second tubular member 130. The second tubular member has a window or opening 132 cut out on one side. In a preferred embodiment, the materials and dimensions of the various components forming the guide wire 120 are as follows. The core wire 122 is formed of a gold plated stainless steel core wire and has a diameter of about 0.007 inches and a length of about 66 inches. The sleeve 126 is formed of an insulating material, preferably polyimide and has a length of about 65 inches. The first tubular member is formed of a plastic and has a length of about 6 inches, an inner diameter of about 0.008 inches and an outer diameter of about 0.017 inches. The second tubular member 130 is formed of stainless steel and has a length of about 1.0 inches, and inner diameter of about 0.012 inches and an outer diameter of about 0.017 inches.

The proximal end of the sensor 100 and the distal end of the core wire 122 are brought in close proximity but preferably are not connected or coupled to one another. The sleeve 126 surrounds and contacts the exterior surface of the core wire 122. The first tubular member 128 surrounds but does not contact a proximal portion of the core wire 122 and sleeve member 126. The second tubular member 130 surrounds the distal portion of the core wire 122 and sleeve 126, the pressure sensor 100 and the extension member 134 of the spring tip 124. An adhesive bonds the extension member 134 of the spring tip 124 in the distal end of the second tubular member 130 so that the coils of the spring tip 124 extend distally from the distal end of the second tubular member 130. A close tolerance fit exists between the exterior of the sensor 100 and the interior of the second tubular member 130 so that the second tubular member 130 keeps the sensor 100 in position. Because the sensor is not coupled or connected to any other elements of the guide wire 120, the forces exerted on it are lessened as the guide wire is delivered to the site of the occlusion.

The leads 105 of the coil 104 are connected to the core wire 122 and first tubular member 128 as was previously described with reference to FIG. 5.

The guide wire 120 is delivered to the occlusion so that the window 132 formed in the second tubular member 130 exposes the sensor 100 to the pressure existing in the vessel or artery proximal to the occlusion and then the guide wire is moved to position the window at a location distal to the occlusion to measure the pressure at that location In another embodiment of the present invention, the non-volatile liquid interface 112 of FIG. 7 may be replaced with a water soluble polymer such as polyehthleneoxide available from the Aldrich Chemical Company of Milwaukee, Wis. The water soluble polymer hardens when it is placed in the tubular member of the sensor and thus forms an interface between the ferrofluid and the environment in which the sensor is placed thus preventing evaporation of the ferrofluid. When used in a patient, the water soluble polymer dissolves and the sensor becomes functional. As an alternative, it would also be preferable to use a ferrofluid which is non-volatile and non-toxic which would obviate the need for the non-volatile or water soluble plugs.

While the sensor has been illustrated as incorporated into guide wires, the pressure sensors 10 and 100 of FIG. 1 and 7 respectively, may be incorporated into other devices and the present invention is not limited to the devices illustrated.

While this invention has been shown and described in connection with the preferred embodiments, it is apparent that certain changes and modifications, in addition to those mentioned above, may be made from the basic features of the present invention. Accordingly, it is the intention of the Applicant to protect all variations and modifications within the true spirit and valid scope of the present invention.

What is claimed is:

1. A pressure sensor comprising:
   a tubular member having a proximal end, a distal end and a window exposing the interior of the tubular member to the exterior of the tubular member wherein the proximal end of the tubular member is sealed;
   a column of ferrofluid partially filling the interior of the tubular member, the ferrofluid column capable of movement within the tubular member in response to external pressure exerted at the window of the tubular member;
   a gaseous column filling the remainder of the interior of the tubular member from the proximal end of the tubular member to the column of ferrofluid; and
   a transducer coupled to the tubular member for detecting the movement of the ferrofluid column in the tubular member and converting the detection to a signal proportional to the external pressure exerted at the window.

2. A pressure sensor according to claim 1 wherein the window is located at the distal end of the tubular member.

3. A pressure sensor according to claim 2 further including a non-volatile liquid between the ferrofluid column and the window of the tubular member.

4. A pressure sensor according to claim 2 further including a water soluble polymer between the ferrofluid column and the window of the tubular member.

5. A pressure sensor according to claim 1 wherein the window is located in the side of the tubular member and the distal end of the tubular member is sealed.

6. A pressure sensor according to claim 5 further including a sheath covering the window formed in the tubular member.

7. A pressure sensor according to claim 1 wherein the transducer comprises:
   a coil wound around the exterior of the tubular member, the coil receiving a constant driving current, whereby movement of the ferrofluid column in the tubular member in response to pressure exerted at the window induces a change in voltage across the coil.

8. A pressure sensor according to claim 7 wherein the coil is formed of silver.

9. A pressure sensor according to claim 4 further including an electronic circuit for applying the constant driving current to the coil and for measuring the voltage across the coil.

10. A pressure sensing system comprising:
    a percutaneous transluminal device having an elongated shaft and a distal end for insertion into a patient's vessel;
    a pressure sensor coupled to the transluminal device for converting pressure at the distal end of the transluminal device into electrical signals, the pressure sensor including a tubular member having a proximal end, a distal end and a window exposing the interior of the tubular member to the exterior of the tubular member, a column of ferrofluid partially filling the interior of the tubular member, the ferrofluid column capable of movement within the tubular member in response to external pressure exerted at the window of the tubular member, a transducer coupled to the tubular member for detecting the movement of the ferrofluid column in the tubular member and converting the detection to an electrical signal proportional to the pressure exerted at the window; and
    processing circuitry coupled to the pressure sensor for processing the electrical signals and coupling the processed signals to a peripheral device, the peripheral device generating a representation of the pressure occurring at the distal end of the transluminal device.

11. The system according to claim 10 wherein the transluminal device is a guide wire.

12. A pressure sensing system according to claim 10 wherein the percutaneous transluminal device has a core wire extending concentrically within the elongated shaft terminating proximally of the distal end of the transluminal device and the pressure sensor is located at the distal end of the core wire so that the pressure sensor is located at the distal end of the transluminal device.

13. A pressure sensing system according to claim 12 wherein the transluminal device has a window formed in the distal end of the shaft exposing the sensor to the exterior of the transluminal device.

14. A pressure sensing system according to claim 12 wherein the pressure sensor is uncoupled from the distal end of the core wire.

15. A pressure sensing system according to claim 12 wherein the pressure sensor includes a coil wound around the exterior of the tubular member, the coil receiving a constant driving current whereby movement of the ferrofluid column in the tubular member in response to pressure exerted at the window indices a change in voltage across the coil.

16. A pressure sensing system according to claim 15 wherein the coil is formed of silver.

17. A pressure sensing system according to claim 12 wherein the window is located at the distal end of the tubular member.

18. A pressure sensing system according to claim 12 wherein the window is located in a side of the tubular member and the distal end of the tubular member is sealed.

19. A method of obtaining information about a patient's anatomy comprising the steps of:

providing a pressure sensor including a tubular member having a proximal end, a distal end and a window exposing the interior of the tubular member to the exterior of the tubular member; a column of ferrofluid partially filling the tubular member, the ferrofluid column capable of movement within the tubular member in response to pressure exerted at the window of the tubular member; and a transducer for converting the movement of the ferrofluid column in the member into a signal proportional to the pressure exerted at the window;

inserting the pressure sensor into the patient's vessel;

positioning the window of the pressure sensor at a desired location;

applying a constant drive current to the transducer;

measuring the voltage across the transducer of the pressure sensor;

converting the measured voltage into a pressure value; and displaying the pressure value.

20. The method of claim 19 wherein said step of providing a pressure sensor includes providing a transducer having a coil wound around the exterior of the tubular member and positioned on the tubular member so as to sense movement of the ferrofluid.

21. A pressure sensing system comprising:

a percutaneous transluminal device having an elongated shaft and a distal end for insertion into a patient's vessel; and a pressure sensor coupled to said transluminal device, said pressure sensor having a column of ferrofluid which is subjected to the pressure at the distal end of the transluminal device and moves in response to that pressure, the pressure sensor also having a detector which detects movement of the ferrofluid and converts that detection to an electrical signal.

* * * * *

UNITED STATES PATENT AND TRADEMARK OFFICE
CERTIFICATE OF CORRECTION

PATENT NO. : 5,450,853
DATED : September 19, 1995
INVENTOR(S) : Roger Hastings et al.

It is certified that error appears in the above-indentified patent and that said Letters Patent is hereby corrected as shown below:

<u>On the Title Page</u>

In column 2, line 1 of the "Attorney, Agent, or Firm" data, delete "Willian, Brinks, Hofer, Gilson & Lione" and substitute --Willian Brinks Hofer Gilson & Lione--.

Col. 10, line 39, delete "4" and substitute --7--.

Col. 12, line 10, after "the" insert --tubular--.

Signed and Sealed this

Second Day of April, 1996

BRUCE LEHMAN

Attest:

Attesting Officer

Commissioner of Patents and Trademarks